(12) United States Patent
Williamson et al.

(10) Patent No.: US 8,201,942 B2
(45) Date of Patent: Jun. 19, 2012

(54) SYSTEM AND METHOD FOR IDENTIFYING A POSITION TO INSERT A SCLERAL PROSTHESIS INTO AN EYE

(75) Inventors: Douglas C. Williamson, Coppell, TX (US); Barrie D. Soloway, Long Beach, NY (US); Gene W. Zdenek, Northridge, CA (US); Gary A. Richardson, Dallas, TX (US)

(73) Assignee: Refocus Group, Inc., Dallas, TX (US)

( * ) Notice: Subject to any disclaimer, the term of this patent is extended or adjusted under 35 U.S.C. 154(b) by 480 days.

(21) Appl. No.: 12/416,868

(22) Filed: Apr. 1, 2009

(65) Prior Publication Data

US 2009/0254071 A1 Oct. 8, 2009

Related U.S. Application Data

(60) Provisional application No. 61/072,757, filed on Apr. 2, 2008.

(51) Int. Cl.
*A61B 3/00* (2006.01)
*A61M 35/00* (2006.01)
(52) U.S. Cl. .......... 351/200; 351/246; 604/294
(58) Field of Classification Search .......... 351/200, 351/247, 246; 604/294; 623/4.1, 623
See application file for complete search history.

(56) References Cited

U.S. PATENT DOCUMENTS

| | | | |
|---|---|---|---|
| 3,609,864 A | 10/1971 | Bassett | |
| 3,922,784 A | 12/1975 | Prince et al. | |
| 4,071,029 A | 1/1978 | Richmond et al. | |
| 4,340,059 A | 7/1982 | Marinoff | |
| 4,601,290 A | 7/1986 | Effron et al. | |
| 4,649,919 A | 3/1987 | Thimsen et al. | |
| 4,665,914 A | 5/1987 | Tanne | |
| 4,672,964 A | 6/1987 | Dee et al. | |
| 4,688,570 A | 8/1987 | Kramer et al. | |
| 4,710,193 A | 12/1987 | Volk | |
| 4,753,655 A | 6/1988 | Hecht | |

(Continued)

FOREIGN PATENT DOCUMENTS

EP 0083494 A1 7/1983

(Continued)

OTHER PUBLICATIONS

Spencer P. Thornton, "Anterior Ciliary Sclerotomy (ACS), A Procedure to Reverse Presbyopia," Surgery for Hyperopia and Presbyopia, 1997, pp. 33-36.

(Continued)

*Primary Examiner* — James Greece (57) ABSTRACT

A method includes identifying an actual location of a ciliary body in a patient's eye. The method also includes identifying a position for a scleral prosthesis to be inserted into scleral tissue of the patient's eye based on the identified location of the ciliary body. The method could also include forming a scleral tunnel in the scleral tissue of the patient's eye based on the identified position and inserting the scleral prosthesis into the scleral tunnel. Identifying the actual location of the ciliary body could include illuminating a first portion of the patient's eye using illumination provided at a second portion of the patient's eye. The illumination provided at the second portion of the patient's eye may be provided through an eyelid of the patient and may travel under a cornea of the patient's eye to the first portion of the patient's eye.

20 Claims, 4 Drawing Sheets

U.S. PATENT DOCUMENTS

| | | | |
|---|---|---|---|
| 4,923,467 A | 5/1990 | Thompson | |
| 4,955,882 A | 9/1990 | Hakky | |
| 4,986,807 A | 1/1991 | Farr | |
| 5,090,955 A | 2/1992 | Simon | |
| 5,098,438 A | 3/1992 | Siepser | |
| 5,188,125 A | 2/1993 | Kilmer et al. | |
| 5,203,865 A | 4/1993 | Siepser | |
| 5,215,104 A | 6/1993 | Steinert | |
| 5,222,959 A | 6/1993 | Anis | |
| 5,342,377 A | 8/1994 | Lazerson | |
| 5,423,841 A | 6/1995 | Kornefeld | |
| 5,431,671 A | 7/1995 | Nallakrishnan | |
| 5,441,510 A | 8/1995 | Simpson et al. | |
| 5,492,528 A | 2/1996 | Anis | |
| 5,522,829 A | 6/1996 | Michalos | |
| 5,571,106 A | 11/1996 | Coufal et al. | |
| 5,624,456 A | 4/1997 | Hellenkamp | |
| 5,653,724 A | 8/1997 | Imonti | |
| 5,779,723 A | 7/1998 | Schwind | |
| 5,817,115 A | 10/1998 | Nigam | |
| 5,891,131 A | 4/1999 | Rajan et al. | |
| 5,908,433 A | 6/1999 | Eager et al. | |
| 6,007,578 A | 12/1999 | Schachar | |
| 6,033,437 A | 3/2000 | Perry | |
| 6,051,009 A | 4/2000 | Hellenkamp et al. | |
| 6,117,149 A | 9/2000 | Sorensen et al. | |
| 6,197,056 B1 * | 3/2001 | Schachar | 623/4.1 |
| 6,231,583 B1 | 5/2001 | Lee | |
| 6,264,668 B1 | 7/2001 | Prywes | |
| 6,328,747 B1 | 12/2001 | Nun | |
| 6,565,584 B1 | 5/2003 | Mathis et al. | |
| 6,602,266 B1 | 8/2003 | Loomas et al. | |
| 6,610,075 B1 | 8/2003 | Levesque et al. | |
| 6,926,727 B2 | 8/2005 | Schachar et al. | |
| 7,189,248 B2 | 3/2007 | Schachar et al. | |
| 2001/0010019 A1 * | 7/2001 | Schachar | 623/4.1 |
| 2002/0077642 A1 | 6/2002 | Patel et al. | |
| 2002/0116062 A1 | 8/2002 | Portney | |
| 2004/0073245 A1 | 4/2004 | Schachar et al. | |
| 2004/0073303 A1 | 4/2004 | Schanzlin et al. | |
| 2007/0268456 A1 | 11/2007 | Ohbayshi et al. | |

FOREIGN PATENT DOCUMENTS

| | | |
|---|---|---|
| JP | 61170449 | 8/1986 |
| WO | WO 94/03129 A1 | 2/1994 |
| WO | WO 94/18636 A2 | 8/1994 |
| WO | WO 98/42409 A1 | 10/1998 |
| WO | WO 99/17684 A1 | 4/1999 |
| WO | WO 99/17691 A1 | 4/1999 |
| WO | WO 99/30645 A2 | 6/1999 |
| WO | WO 99/30656 A1 | 6/1999 |
| WO | WO 00/74600 A1 | 12/2000 |
| WO | WO 01/45607 A1 | 6/2001 |
| WO | WO 2005/034730 A2 | 4/2005 |
| WO | WO 2007/087061 A2 | 8/2007 |

OTHER PUBLICATIONS

Translation of Office Action issued on Feb. 8, 2008 in Japanese Patent Application No. 2002-567203.

Office Action dated May 13, 2009 in connection with U.S. Appl. No. 11/698,008.

Office Action dated Apr. 8, 2009 in connection with U.S. Appl. No. 11/606,480.

Office Action dated Jul. 1, 2009 in connection with U.S. Appl. No. 11/323,284.

Michael R. Bryant et al., "Computer-Aided Surgical Design in Refractive Keratotomy", The CLAO Journal, vol. 13, No. 4, Jul. 1987, pp. 238-242.

Notice of Transmittal of the International Search Report or the Declaration dated Mar. 6, 2008 in PCT Application No. PCT/US03/15896.

Notification of Transmittal of the International Search Report and the Written Opinion of the International Searching Authority, or the Declaration dated Jun. 30, 2009 in connection with PCT Application No. PCT/US09/39341.

Mr. P. Agrawal, et al., "Ciliary Body Position Variability in Glaucoma Patients as Assessed by Scleral Transillumination", 2007, 3 pages.

Office Action dated Sep. 22, 2009 in connection with U.S. Appl. No. 11/323,283.

"The Surgical Armamentarium", (*American v. Mueller*), 1980, p. 4, Fig. C.

Supplementary European Search Report dated Apr. 17, 2012 in connection with European Patent Application No. EP 09 72 8537.

* cited by examiner

SYSTEM AND METHOD FOR IDENTIFYING A POSITION TO INSERT A SCLERAL PROSTHESIS INTO AN EYE

CROSS-REFERENCE TO RELATED PATENT DOCUMENTS

This application claims priority under 35 U.S.C. §119(e) to U.S. Provisional Patent Application No. 61/072,757 filed on Apr. 2, 2008, which is hereby incorporated by reference.

This application is related to the following U.S. patent applications and issued patents:
(1) U.S. Pat. No. 6,007,578 entitled "Scleral Prosthesis for Treatment of Presbyopia and Other Eye Disorders" issued on Dec. 28, 1999;
(2) U.S. Pat. No. 6,280,468 entitled "Scleral Prosthesis for Treatment of Presbyopia and Other Eye Disorders" issued on Aug. 28, 2001;
(3) U.S. Pat. No. 6,299,640 entitled "Scleral Prosthesis for Treatment of Presbyopia and Other Eye Disorders" issued on Oct. 9, 2001;
(4) U.S. Pat. No. 5,354,331 entitled "Treatment of Presbyopia and Other Eye Disorders" issued on Oct. 11, 1994;
(5) U.S. Pat. No. 5,465,737 entitled "Treatment of Presbyopia and Other Eye Disorders" issued on Nov. 14, 1995;
(6) U.S. Pat. No. 5,489,299 entitled "Treatment of Presbyopia and Other Eye Disorders" issued on Feb. 6, 1996;
(7) U.S. Pat. No. 5,503,165 entitled "Treatment of Presbyopia and Other Eye Disorders" issued on Apr. 2, 1996;
(8) U.S. Pat. No. 5,529,076 entitled "Treatment of Presbyopia and Other Eye Disorders" issued on Jun. 25, 1996;
(9) U.S. Pat. No. 5,722,952 entitled "Treatment of Presbyopia and Other Eye Disorders" issued on Mar. 3, 1998;
(10) U.S. Pat. No. 6,197,056 entitled "Segmented Scleral Band for Treatment of Presbyopia and Other Eye Disorders" issued on Mar. 6, 2001;
(11) U.S. Pat. No. 6,579,316 entitled "Segmented Scleral Band for Treatment of Presbyopia and Other Eye Disorders" issued on Jun. 17, 2003;
(12) U.S. Pat. No. 6,926,727 entitled "Surgical Blade for Use with a Surgical Tool for Making Incisions for Scleral Eye Implants" issued on Aug. 9, 2005;
(13) U.S. Pat. No. 6,991,650 entitled "Scleral Expansion Device Having Duck Bill" issued on Jan. 31, 2006;
(14) U.S. patent application Ser. No. 10/080,877 entitled "System and Method for Making Incisions for Scleral Eye Implants" filed on Feb. 22, 2002;
(15) U.S. patent application Ser. No. 10/443,122 entitled "System and Method for Determining a Position for a Scleral Pocket for a Scleral Prosthesis" filed on May 20, 2003;
(16) U.S. patent application Ser. No. 11/137,085 entitled "Scleral Prosthesis for Treatment of Presbyopia and Other Eye Disorders" filed on May 24, 2005;
(17) U.S. patent application Ser. No. 11/199,591 entitled "Surgical Blade for Use with a Surgical Tool for Making Incisions for Scleral Eye Implants" filed on Aug. 8, 2005;
(18) U.S. patent application Ser. No. 11/252,369 entitled "Scleral Expansion Device Having Duck Bill" filed on Oct. 17, 2005;
(19) U.S. patent application Ser. No. 11/323,283 entitled "Surgical Blade for Use with a Surgical Tool for Making Incisions for Scleral Eye Implants" filed on Dec. 30, 2005;
(20) U.S. patent application Ser. No. 11/323,284 entitled "System and Method for Making Incisions for Scleral Eye Implants" filed on Dec. 30, 2005;
(21) U.S. patent application Ser. No. 11/322,728 entitled "Segmented Scleral Band for Treatment of Presbyopia and Other Eye Disorders" filed on Dec. 30, 2005;
(22) U.S. patent application Ser. No. 11/323,752 entitled "Segmented Scleral Band for Treatment of Presbyopia and Other Eye Disorders" filed on Dec. 30, 2005;
(23) U.S. Provisional Patent Application No. 60/819,995 entitled "Apparatuses, Systems, and Methods Related to Treating Presbyopia and Other Eye Disorders" filed on Jul. 11, 2006;
(24) U.S. patent application Ser. No. 11/827,444 entitled "Apparatus and Method for Securing Ocular Tissue" filed on Jul. 11, 2007;
(25) U.S. patent application Ser. No. 11/827,382 entitled "Scleral Prosthesis for Treating Presbyopia and Other Eye Disorders and Related Devices and Methods" filed on Jul. 11, 2007;
(26) U.S. Provisional Patent Application No. 61/001,593 entitled "Apparatuses and Methods for Forming Incisions in Ocular Tissue" filed on Nov. 2, 2007;
(27) U.S. patent application Ser. No. 12/260,694 entitled "Apparatuses and Methods for Forming Incisions in Ocular Tissue" filed on Oct. 29, 2008; and
(28) U.S. Provisional Patent Application No. 61/065,149 entitled "Scleral Prosthesis for Ocular Drug Delivery to Treat Glaucoma, Macular Degeneration, and Other Eye Disorders or Diseases and Related Method" filed on Feb. 8, 2008.

All of these patents and patent applications are hereby incorporated by reference.

TECHNICAL FIELD

This disclosure is generally directed to the treatment of presbyopia, hyperopia, primary open angle glaucoma, ocular hypertension, and other eye disorders. More specifically, this disclosure is directed to a system and method for identifying a position to insert a scleral prosthesis into an eye.

BACKGROUND

It is possible to treat presbyopia, glaucoma, and other eye disorders by implanting scleral prostheses within the sclera of a patient's eye. For each individual scleral prosthesis, an incision is made in the sclera of the patient's eye. The incision is then extended under the surface of the sclera to form a scleral "tunnel," and a scleral prosthesis is placed within the tunnel. One or multiple scleral prostheses may be implanted in a patient's eye to (among other things) treat presbyopia, glaucoma, ocular hypertension, elevated intraocular pressure, macular degeneration, or other eye disorders. This technique is described more fully in the patents documents incorporated by reference above.

SUMMARY

This disclosure provides a system, apparatus, method, and computer program for identifying a position to insert a scleral prosthesis into an eye.

In a first embodiment, a method includes identifying an actual location of a ciliary body in a patient's eye. The method also includes identifying a position for a scleral prosthesis to be inserted into scleral tissue of the patient's eye based on the identified location of the ciliary body.

In particular embodiments, the method further includes forming a scleral tunnel in the scleral tissue of the patient's eye based on the identified position and inserting the scleral prosthesis into the scleral tunnel.

In a second embodiment, a system includes eye measurement equipment configured to generate information associated with an actual location of a ciliary body in a patient's eye. The system also includes a controller configured to use the information from the eye measurement equipment to identify a position for a scleral prosthesis to be inserted into scleral tissue of the patient's eye based on the identified location of the ciliary body.

In a third embodiment, an apparatus includes a controller configured to identify a position for a scleral prosthesis to be inserted into scleral tissue of a patient's eye. The controller is configured to identify the position for the scleral prosthesis using an actual location of a ciliary body in the patient's eye.

In a fourth embodiment, a computer readable medium embodies a computer program. The computer program includes computer readable program code for receiving information identifying an actual location of a ciliary body in a patient's eye. The computer program also includes computer readable program code for identifying a position for a scleral prosthesis to be inserted into scleral tissue of the patient's eye based on the actual location of the ciliary body.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
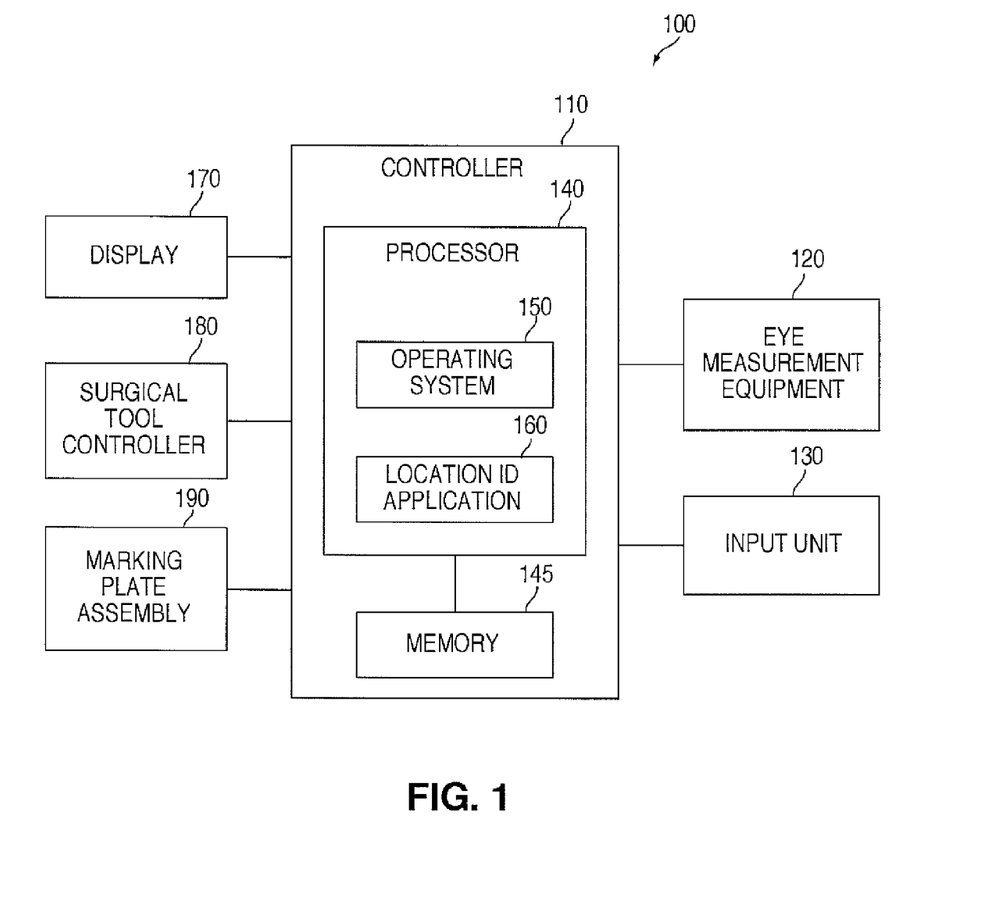
FIG. 1 illustrates an example system for identifying a position to insert a scleral prosthesis into an eye in accordance with this disclosure.

FIG. 1 illustrates an example system 100 for identifying a position to insert a scleral prosthesis into an eye in accordance with this disclosure. The embodiment of the system 100 shown in FIG. 1 is for illustration only. Other embodiments of the system 100 could be used without departing from the scope of this disclosure.

As shown in FIG. 1, the system 100 includes a controller 110, which could be coupled to eye measurement equipment 120. The controller 110 could receive eye measurements from the eye measurement equipment 120. The eye measurements could, for example, include an identification of the position of a ciliary body in each quadrant of a patient's eye. The controller 110 could then use this information in any suitable manner.

The eye measurement equipment 120 includes any suitable component(s) for taking measurements related to, or otherwise assisting in the identification of, the location of a ciliary body in one or more areas of a patient's eye. For example, the eye measurement equipment 120 could include transillumination or retroillumination equipment used to illuminate the patient's eye. Transillumination generally involves directly illuminating one portion of the patient's eye through the sclera and beneath the cornea of the eye, or through any other portion of the patient's eye (and possibly through one of the patient's eyelids). Retroillumination generally involves indirectly illuminating one portion of the patient's eye through the sclera and beneath the cornea of the eye by reflecting light off the back of the eye to illuminate an image on the opposing quadrant of the eye opposite the light source. As a particular example, the eye measurement equipment 120 could include a very bright light source (such as a filtered or unfiltered visible spectrum fiber optic normal or cold light source or any other suitable light source) and optics or other components for delivering the light to different areas of the patient's eye (such as an ACMI/STORZ surgical fiber optic endoscope). The eye measurement equipment 120 could also include components supporting other imaging techniques for locating the ciliary body in one or more areas of a patient's eye, such as components that support optical coherence tomography (OCT), ultrasound biomicroscopy (UBM), magnetic resonance imaging (MRI), or any other suitable imaging techniques.

The controller 110 could also be coupled to an input unit 130. The controller 110 could receive any suitable input data through the input unit 130. The input data could, for example, include an identification of the position of a ciliary body in each quadrant of a patient's eye. The input data could also include other surgical parameters or any other suitable data. The input data could be provided by a surgeon or other personnel using the system 100. The input unit 130 includes any suitable component(s) for providing input to the controller 110. The input unit 130 could, for instance, include a keypad, keyboard, mouse, or other or additional input device(s).

In this example, the controller 110 includes a processor 140 configured to perform various functions to facilitate the implantation of one or more scleral prostheses in a patient's eye. The processor 140 is capable of executing instructions stored in a memory 145 within the controller 110. For example, the processor 140 could execute an operating system 150 and a location identification application 160 (which could be stored in the memory 145). The location identification application 160 could represent a software application or other computer instructions that perform various calculations to identify one or more locations for inserting one or more scleral prostheses into a patient's eye.

In some embodiments, the location identification application 160 can receive measured parameters of an eye that are provided by the eye measurement equipment 120 and/or input by a user through the input unit 130. The location identification application 160 can use this data to identify the one or more locations for inserting one or more scleral prostheses into the patient's eye. For example, the location identification application 160 could identify locations for inserting scleral prostheses into the patient's eye based on the identified locations of the ciliary body in four different quadrants of the patient's eye (obtained during transillumination, retroillumination, or other technique). The identified locations could represent the locations where scleral pockets or tunnels are to be formed in the scleral tissue of the patient's eye. Additional details regarding the identification of locations for inserting scleral prosthesis into a patient's eye are provided below.

The processor 140 includes any suitable component(s) for identifying one or more locations for inserting one or more scleral prostheses into a patient's eye. The processor 140 could, for example, represent a microprocessor, microcontroller, digital signal processor, application specific integrated circuit (ASIC), or other processing or computing device. The memory 145 includes any suitable volatile or non-volatile storage and retrieval device or devices.

The identified location(s) for inserting one or more scleral prostheses into a patient's eye could then be used in any suitable manner. For example, the identified location(s) could be presented to a surgeon or other personnel on a display 170 for review. The display 170 includes any suitable component for displaying information, such as a liquid crystal display (LCD) or cathode ray tube (CRT) display.

The identified location(s) for inserting one or more scleral prostheses into a patient's eye could also be provided to a surgical tool controller 180. The surgical tool controller 180 controls the operation of a surgical tool, such as a tool for forming scleral pockets or tunnels in a patient's eye. The information provided by the controller 110 to the surgical tool controller 180 could enable the surgical tool controller 180 to form scleral pockets or tunnels in the identified location(s) of the patient's eye. As a particular example, the surgical tool controller 180 may use the information from the location identification application 160 to automatically determine an incision point for an incision (where the incision creates a scleral pocket or tunnel). Any suitable surgical tool could be controlled by the surgical tool controller 180. Examples of surgical tools for forming scleral pockets or tunnels are disclosed in various ones of the patent documents incorporated by reference above. The surgical tool controller 180 includes any suitable component(s) for controlling one or more surgical tools.

In addition, the identified location(s) for inserting one or more scleral prostheses into a patient's eye could be provided to a marking plate assembly 190. The marking plate assembly 190 can form marks on a patient's eye. For example, the marking plate assembly 190 could make marks on a patient's eye to identify the locations of scleral pockets or tunnels to be formed in the patient's eye. The marks could be used by a surgeon or other personnel, such as when a surgeon manually forms the scleral pockets or tunnels or when the surgeon uses the marks to place a surgical tool on the patient's eye. The marking plate assembly 190 could also act as a template to guide a surgical cutting device to a proper location, similar to or including certain fixation tools disclosed in the patent documents incorporated by reference above. The marking plate assembly 190 could further be customized for a particular patient based on measurements of that patient's eye(s). The marking plate assembly 190 includes any suitable component(s) for making marks on a patient's eye and/or for guiding a surgical cutting device.

Although FIG. 1 illustrates one example of a system 100 for identifying a position to insert a scleral prosthesis into an eye, various changes may be made to FIG. 1. For example, the functional division shown in FIG. 1 is for illustration only. Various components in FIG. 1 could be combined, further subdivided, or omitted and additional components could be added according to particular needs. As a particular example, the eye measurement equipment 120 could be omitted if personnel manually measure the locations of the ciliary body and enter the locations through the input unit 130. As another particular example, the surgical tool controller 180 could be omitted if the identified locations of scleral pockets or tunnels are only used to mark the patient's eye using the marking plate assembly 190. Also, FIG. 1 illustrates one example system 100 where transillumination, retroillumination, or other technique could be used to identify a position of the ciliary body in the eye so that a location of a scleral prosthesis can be determined. These techniques could be used with any other suitable system, or they could be performed manually.

Figure 2:
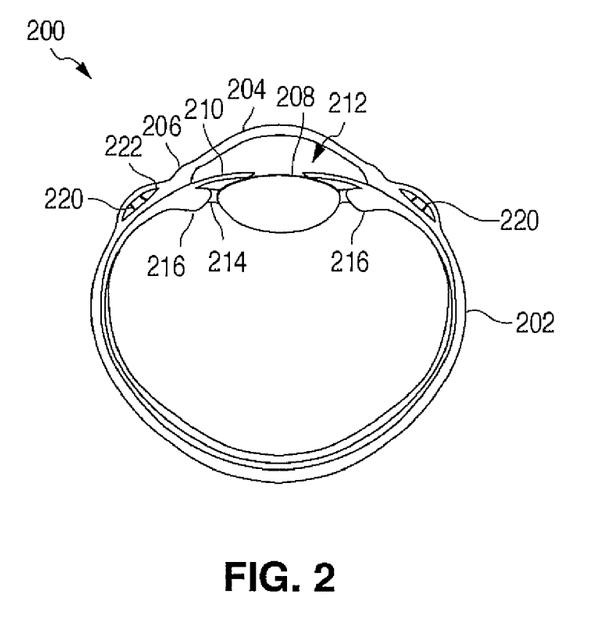
FIG. 2 illustrates an example implantation of a scleral prosthesis into an eye in accordance with this disclosure.

FIG. 2 illustrates an example implantation of a scleral prosthesis into an eye in accordance with this disclosure. The example implantation shown in FIG. 2 is for illustration only. Other implantations of scleral prostheses could be performed without departing from the scope of this disclosure.

As shown in FIG. 2, an eye 200 includes the white, tough sclera 202 and the cornea 204. The generally circular junction of the cornea 204 and the sclera 202 is the limbus 206. The outline of the limbus 206 is easily identified because this is where the dark part of the eye (caused by the pigment in the iris 210 reflecting through the cornea 204) becomes white as the cornea 204 transitions into the white of the sclera 202. Within the globe of the eye, a crystalline lens 208 is enclosed in a thin membranous capsule and is located immediately posterior to the iris 210, suspended centrally posterior to the pupil 212 on the optical axis of the eye. The lens 208 is suspended by zonules 214, which extend between the capsule of the lens 208 and the ciliary body 216. The ciliary body 216 lies just under the sclera 202 (just inwardly of the sclera 202) and is attached to the inner surface of the sclera 202.

Changes in the shape of the ciliary body 216 (and in particular the ciliary muscle within the ciliary body) cause corresponding changes in the shape of the lens 208 when the effective working distance between the ciliary body 216 and the lens 208 is satisfactory (such as in a young eye). In these circumstances (i.e. a young eye), changes in the shape of the ciliary body 216 allow the lens 208 to become more convex, allowing the eye to accommodate or see "at near" (close up). As the eye ages, the effective working distance between the lens 208 and the ciliary body 216 diminishes, and the eye loses its ability to accommodate (this condition is called presbyopia).

As described in more detail in the patent documents incorporated by reference above, the effective working distance of the ciliary muscle of the eye can be increased by inserting one or more scleral prostheses 220 into one or more scleral pockets or tunnels 222 formed in the sclera 202. This can be done to help treat presbyopia, glaucoma, ocular hypertension, elevated intraocular pressure, macular degeneration, or other eye disorders. Any suitable scleral prosthesis 220 can be implanted into the sclera 202 of the eye 200. For example, different scleral prostheses are disclosed in various ones of the patent documents incorporated by reference above.

The placement of a scleral prosthesis 220 with respect to the ciliary body 216 can have a large influence on the effectiveness of the scleral prosthesis 220 in restoring the effective working distance between the lens 208 and the ciliary body 216. For example, the beginning or anterior edge of the ciliary body 216 can generally be found 1.0-5.0 millimeters posterior to the limbus 206 in any give quadrant, with the balance of the ciliary body 216 moving posteriorly along the intraocular surface of the sclera 202 for approximately 5.0-7.0 millimeters. However, patients often show some degree of variability in the distance between the limbus 206 and the beginning of the ciliary body 216 in their eyes 200. This variability can exist between patients and actually within the same patient, such as when this distance varies between quadrants of the same patient's eye(s) 200. In other words, the ciliary muscle is not necessarily symmetrical and can vary patient by patient, eye by eye, and quadrant by quadrant. This variation can sometimes be significant, such as when the distance to the forward edge of the ciliary body 216 is 2.0 mm posterior to the limbus 206 in one quadrant and 5.0 mm to the forward edge of the ciliary body 216 in another quadrant (possibly within the same eye).

Because of this variation, the corrective effect provided by a scleral prosthesis 220 could vary depending on the placement of the scleral prosthesis 220 within the eye 200. For example, if the scleral prosthesis 220 is implanted at a location that is quite far from the ciliary body 216 (as defined by its forward edge) in a particular quadrant of the eye 200, the corrective effect provided by the scleral prosthesis 220 can be reduced. In contrast, if the scleral prosthesis 220 is implanted at a location that is relatively close to the ciliary body 216 in a particular quadrant of the eye 200, the corrective effect provided by the scleral prosthesis 220 can be greater.

In accordance with this disclosure, the actual location of at least part of the ciliary body 216 in the eye 200 (such as its forward or anterior edge) can be determined or estimated with relatively high accuracy. For example, the actual location of the ciliary body 216 in each of the four quadrants of the eye 200 can be determined or estimated. With the actual location of the ciliary body 216 known or estimated with higher accuracy, more optimal locations of the scleral prostheses 220 can be determined. For instance, the scleral prostheses 220 could be implanted so that they are no more than 1.0 mm-1.25 mm away from the forward edge of the ciliary body 216 of the eye 200, with the scleral prostheses 220 being posterior to the forward edge of the ciliary body 216. Of course, other distances can be used, such as between 2.0 mm and 4.0 mm. The desired distance between the ciliary body 216 and a scleral prosthesis 220 could be based on a number of factors, including a size and a thickness of the scleral prosthesis 220. In particular embodiments, thicker scleral prostheses 220 could be used, such as those having a thickness of approximately 2.5 mm, or longer scleral prosthesis, such as those having a length of approximately 7.0 mm. In other particular embodiments, it may be appropriate to locate the scleral prostheses 220 on or anterior to the forward edge of the ciliary body 216, such as at fixed locations.

Whatever the desired distance from the ciliary body 216 to the scleral prosthesis 220 is, this distance can be more accurately obtained by identifying the location of the ciliary body 216 (such as its forward or anterior edge) in the eye 200 prior to implantation of the scleral prosthesis 220. Any suitable technique could be used to identify the location of the ciliary body 216 in a patient's eye 200, such as OCT, UBM, MRI, transillumination, or retroillumination.

Figure 3:
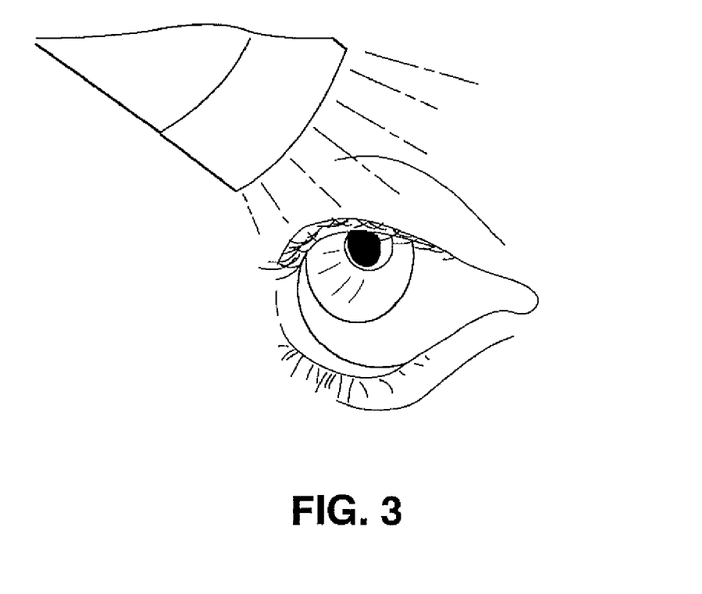
FIG. 3 illustrates an example transillumination of an eye in accordance with this disclosure.

FIG. 3 illustrates an example transillumination of an eye in accordance with this disclosure. During transillumination or retroillumination, one quadrant or other portion of the patient's eye can be illuminated through the sclera and beneath the patient's cornea or from another portion of the eye. As shown in FIG. 3, the superior nasal quadrant of the patient's eye (the upper inner portion of the eye) is being illuminated with light directed into the inferior temporal quadrant of the patient's eye (the lower outer portion of the eye) through the patient's upper eyelid.

During transillumination or retroillumination, the light creates an elliptical shadow around the limbus 206 of the patient's eye 200, which as shown in FIG. 3 is several millimeters outside of the limbus 206. The elliptical shadow is caused by the ciliary body 216 of the eye 200. As a result, the shadow formed in a particular quadrant of the patient's eye 200 can be used to identify the location of the ciliary body 216 in that quadrant. A mark can be placed on the patient's eye 200 in the location where the shadow begins on the sclera 202. After that, the distance between the marked location of the forward edge of the ciliary body 216 and the limbus 206 can be measured, such as by using calipers under normal illumination. The marked location of the forward edge of the ciliary body 216 could also be used to identify a desired location for a scleral prosthesis 220, such as by identifying a location that is 1.0 mm-4.0 mm posterior to the marked location of the ciliary body 216.

In this way, the actual location of the forward edged of the ciliary body 216 can be identified in a non-invasive manner. This can allow more accurate placement of scleral prostheses 220 in a patient's eye 200, which could result in improved corrective effect and better resulting eyesight in the patient.

Although FIG. 2 illustrates one example of an implantation of a scleral prosthesis into an eye, various changes may be made to FIG. 2. For example, any number of scleral prostheses could be inserted into a patient's eye, and each of the scleral prostheses could have any suitable size and shape. Although FIG. 3 illustrates one example of the transillumination of an eye, various changes may be made to FIG. 3. For instance, as noted above, FIG. 3 illustrates the transillumination of one quadrant or other portion of the patient's eye. This transillumination could be repeated for all quadrants or other portions of the patient's eye. Also, retroillumination or any other suitable imaging technique could be used to illuminate the position of the ciliary body in individual quadrants of the eye.

Figure 4:
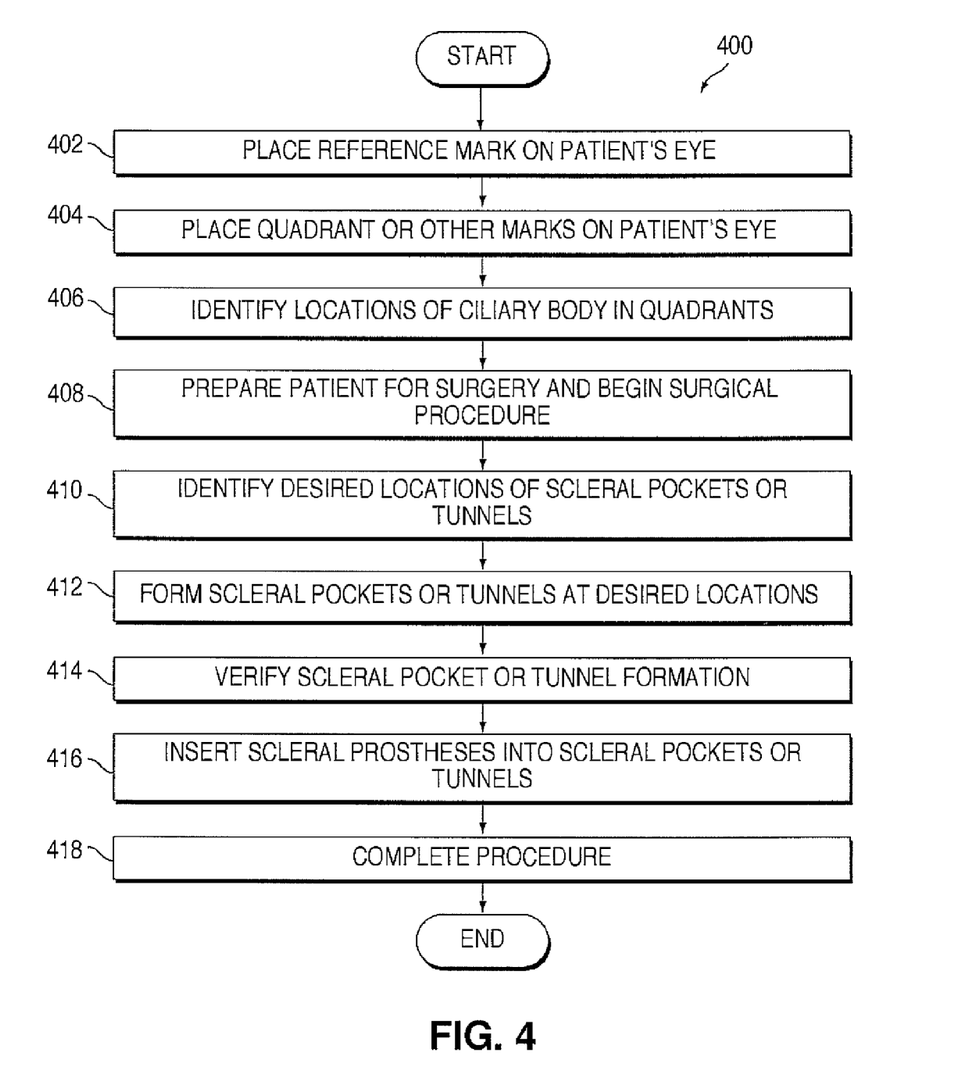
FIG. 4 illustrates an example method for identifying a position to insert a scleral prosthesis into an eye in accordance with this disclosure.

FIG. 4 illustrates an example method 400 for identifying a position to insert a scleral prosthesis into an eye in accordance with this disclosure. The embodiment of the method 400 shown in FIG. 4 is for illustration only. Other embodiments of the method 400 could be used without departing from the scope of this disclosure.

As shown in FIG. 4, the method 400 includes placing a reference mark on a patient's eye at step 402. This could include, for example, a surgeon or other personnel using a surgical pen or other device to place a mark in a desired location on the patient's eye. As a particular example, this could include the surgeon or other personnel placing a reference mark on the sclera of the patient's eye at either the "12 o'clock" position or the "6 o'clock" position.

Quadrant marks are placed on the patient's eye at step 404. The quadrant marks could represent marks formed in the four quadrants of the patient's eye, such as at 45°, 135°, 225°, and 315° (as measured from the reference mark). In particular embodiments, a marking device with a number of possible marking lines could be used, and ink can be placed on the four marking lines to be used to mark the four quadrants of the patient's eye. The marking device could also include a slot and a reticle allowing the surgeon or other personnel to generally align the marking device with the center of the patient's eye and with the reference mark previously placed on the patient's eye. Any other or additional marks could also be placed on the patient's eye, such as clockwise or counter-clockwise marks indicating the direction in which the scleral tunnels or pockets are to be formed by the surgeon.

The locations of the ciliary body in the quadrants of the patient's eye are identified at step 406. This could include, for example, performing a transillumination or retroillumination of the patient's eye 200 to identify the location of the ciliary body 216 in each quadrant of the patient's eye 200. The identified locations could be measured or recorded in any suitable manner, such as by measuring the distance of the ciliary body 216 from the limbus 206 in each quadrant or measuring the distance of the ciliary body 216 from the end of the quadrant mark in each quadrant. The distance from the ciliary body 216 can also be measured to any other suitable marker of a marking system, such as one representing a consistent distance from the center of the eye or the limbus.

The patient is prepared for surgery and the surgical procedure begins at step 408. This could include, for example, taking steps necessary or required to perform ocular surgery, such as placement of the patient and the administration of one or more medications. This could also include performing a peritomy or other conjunctival dissection in order to gain access to the sclera 202 of the patient's eye 200.

The desired locations of scleral pockets or tunnels are identified at step 410, and the scleral pockets or tunnels are formed at step 412. This could include, for example, using the identified location of the ciliary body 216 in each quadrant of the patient's eye 200 to identify the desired locations of scleral pockets or tunnels 222. The desired locations of the scleral pockets or tunnels 222 could be determined in any suitable manner.

If the scleral pockets or tunnels 222 are going to be formed manually, the desired locations of the scleral pockets or tunnels 222 could be determined as follows. The distance between the limbus 206 and the identified location of the ciliary body 216 in each quadrant is measured, such as by using calipers. A specified distance (such as 1 mm) is then added to the measured distance to produce a desired distance. The desired distance, when measured from the limbus 206 (or any other suitable marker) along the quadrant mark for that quadrant (such as by using calipers), defines a point that represents the middle of the anterior edge of the scleral pocket or tunnel 222. A table top marker or other indicator could then be placed across and posterior to that point in order to define the location of the scleral pocket or tunnel 222. At this point, the scleral pocket or tunnel 222 could be formed manually, such as by using a curved or straight cutting blade. This process could then be repeated for each additional scleral pocket or tunnel 222 to be formed.

If the scleral pockets or tunnels 222 are going to be formed using an automated tool, the automated tool typically includes a footplate used to secure the tool on the patient's eye. The footplate could include twist picks, locking dual fixation forceps, or other locking mechanisms for securing the footplate in place on the patient's eye. Details of example footplates can be found in various ones of the patent documents incorporated by reference above. In these situations, the desired locations of the scleral pockets or tunnels 222 could be determined as follows. The distance from the anterior edge of the footplate to the anterior edge of the scleral pocket or tunnel 222 is calculated (based on the structure of the footplate). A specified distance (such as 1 mm) is subtracted from this calculated distance, and the resulting value is added to the measured distance between the limbus 206 (or any other suitable marker) and the identified location of the ciliary body 216 in a particular quadrant. The sum determined here identifies a point along a quadrant mark that represents the position of the middle of the anterior edge of the scleral pocket or tunnel 222. The desired locations of the twist picks, locking dual fixation forceps, or other locking mechanisms are then determined (such as by extending the identified point to form a line that is tangent to the limbus 206 and identifying the desired locations along the tangent line). Note that this depends on the structure of the surgical tool's footplate and the placement of the locking mechanisms on the footplate. Once the desired locations of the locking mechanisms are identified, the surgical tool can be placed in the appropriate position so that the locking mechanisms are located at the desired locations. The locking mechanisms can then be engaged to lock the surgical tool in place, and the surgical tool can be used to form a scleral pocket or tunnel 222. This process could then be repeated for each additional scleral pocket or tunnel 222 to be formed.

The scleral pockets or tunnels that have been formed are then verified at step 414. This could include, for example, measuring the length of the scleral pockets or tunnels 222 to verify that they have a desired length. This could also include measuring the position of each scleral pocket or tunnel 222 from the identified location of the ciliary body 216 in each quadrant of the patient's eye 200. This can be done to help ensure that the scleral pockets or tunnels 222 are formed at desired distances from the identified locations of the ciliary body 216.

If the scleral pockets or tunnels are acceptable, scleral prostheses are inserted into the scleral pockets or tunnels at step 416. This could include, for example, using a feeder tube or other instrument to place a scleral prosthesis 220 into a scleral pocket or tunnel 222. The surgical procedure is then completed at step 418. This could include, for example, placing locking inserts in the scleral prostheses or placing sutures in the patient's eye or otherwise completing the procedure and preparing the patient for recovery.

Although FIG. 4 illustrates one example of a method 400 for identifying a position to insert a scleral prosthesis into an eye, various changes may be made to FIG. 4. For example, while shown as a series of steps, various steps in FIG. 4 could overlap, occur in parallel, occur in a different order, or occur multiple times. As a particular example, the steps shown in FIG. 4 could be repeated twice, once for each eye 200 of the patient. As another particular example, a surgical tool could form a scleral pocket or tunnel 222 and then insert a scleral prosthesis 220 into the scleral pocket or tunnel 222 during a single operation. In addition, the method 400 could be used to identify a single location for a single scleral prosthesis 220 or multiple locations for multiple scleral prostheses 220.

Figure 5:
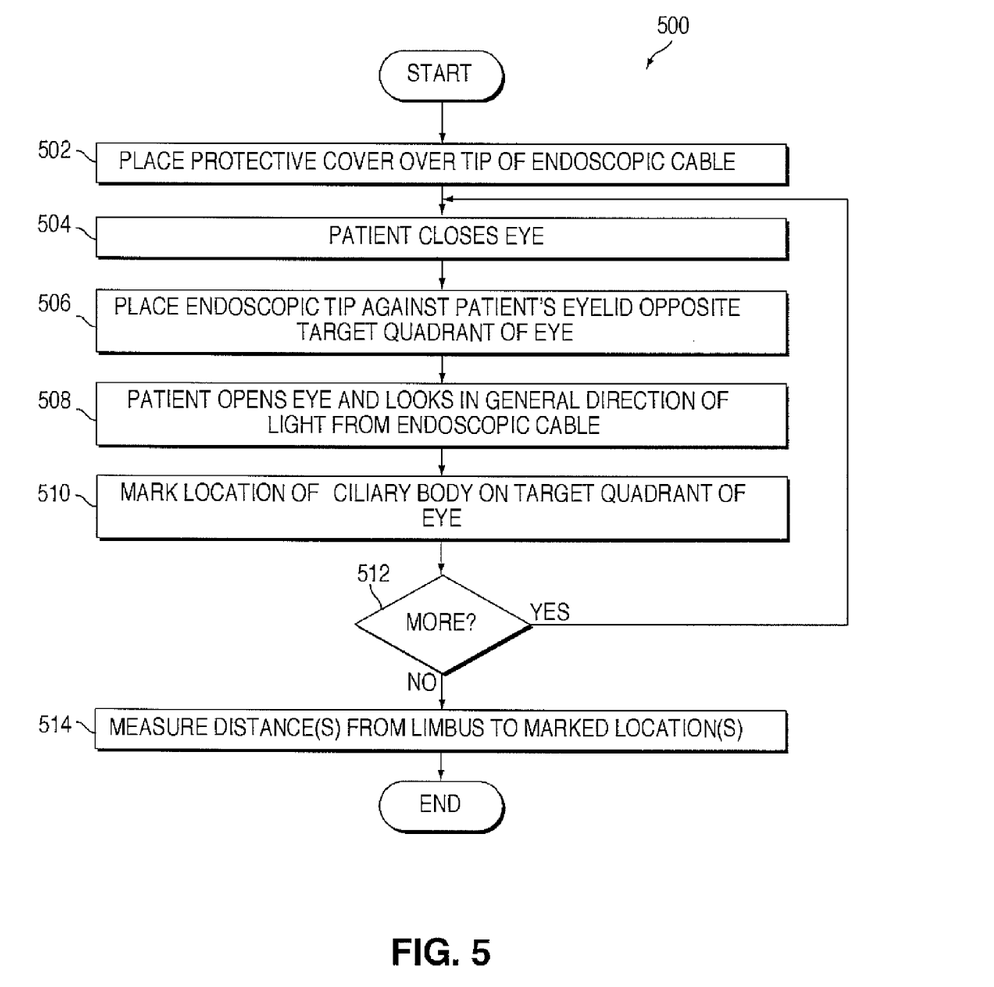
FIG. 5 illustrates an example method for using transillumination or retroillumination to identify a position of a ciliary body in an eye in accordance with this disclosure.

FIG. 5 illustrates an example method 500 for using transillumination or retroillumination to identify a position of a ciliary body in an eye in accordance with this disclosure. The method 500 could, for example, be used during step 406 in the method 400 of FIG. 4 (although other techniques could be used during step 406). The embodiment of the method 500 shown in FIG. 5 is for illustration only. Other embodiments of the method 500 could be used without departing from the scope of this disclosure.

As shown in FIG. 5, a protective cover is placed over the tip of an endoscopic cable at step 502. This could include, for example, placing tape, a silicone sheathe, or a hollow steel tube over the tip of the endoscopic cable. The protective cover generally protects a patient's eye from heat generated by the endoscopic cable.

The patient closes his or her eye at step 504, and the tip of the endoscopic cable is placed against the patient's eye at step 506. This could include, for example, placing the tip of the endoscopic cable against the patient's eyelid in a location that is opposite the quadrant to be examined. As a particular example, the tip of the endoscopic cable could be placed against the patient's eyelid at the inferior nasal quadrant of the patient's eye when the superior temporal quadrant of the patient's eye is being examined. At this point, the patient opens his or her eye at step 508. This could include asking the patient to look straight forward or in any other direction which gives optimal illumination of the ciliary body in the quadrant opposing the light source.

The light from the endoscopic cable forms a shadow within the patient's eye, which is caused by the ciliary body of the patient's eye. The beginning of the shadow represents the forward or anterior edge of the ciliary body 216, with the balance of the ciliary body 216 moving posteriorly along the intraocular surface of the sclera 202 (such as for approximately 5.0-7.0 millimeters). For the purposes of this disclosure, the forward or anterior edge of the ciliary body 216 is used as the central point of reference for analysis in determining placement of the scleral prostheses 220. However, any other suitable portion of the ciliary body 216 could be used as a reference in certain applications. The location of the ciliary body in the target quadrant of the patient's eye, as determined by the forward edge, is then marked on the sclera at step 510. This could include, for example, marking the location where the shadow becomes abruptly dark on the sclera 202 in the target quadrant of the patient's eye 200. The mark could be placed along a suitable "clock hour" on the patient's eye 200, such as along a quadrant mark previously placed on the patient's eye.

If another location of the ciliary body of the patient's eye is to be determined (such as in another quadrant) at step 512, the method 500 returns to step 504. Otherwise, the distance between the limbus and each marked location of the ciliary body is measured at step 514. This could include, for example, measuring the distance between the limbus 206 and each marked location of the ciliary body 216 using a caliper. This may also include measuring the distance(s) using normal illumination and a surgical microscope. At this point, the location of the ciliary body 216 in each quadrant or other portion of the patient's eye is known with relatively high accuracy.

Although FIG. 5 illustrates one example of a method 500 for using transillumination or retroillumination to identify a position of a ciliary body in an eye, various changes may be made to FIG. 5. For example, while shown as a series of steps, various steps in FIG. 5 could overlap, occur in parallel, occur in a different order, or occur multiple times. As a particular example, the steps shown in FIG. 5 could be repeated twice, once for each eye of the patient. Also, the method 500 could be used to identify a single location of the ciliary body 216 or multiple locations of the ciliary body 216.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory ("ROM"), random access memory ("RAM"), a hard disk drive, a compact disc ("CD"), a digital video disc ("DVD"), or any other type of memory.

It may be advantageous to set forth definitions of certain words and phrases used throughout this patent document. The terms "include" and "comprise," as well as derivatives thereof, mean inclusion without limitation. The term "or" is inclusive, meaning and/or.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
  identifying an actual location of a ciliary body in a patient's eye by (i) illuminating a first portion of the patient's eye using illumination provided at a second portion of the patient's eye and (ii) identifying a shadow formed by the ciliary body in the patient's eye; and
  identifying a position for a scleral prosthesis to be inserted into scleral tissue of the patient's eye based on the identified location of the ciliary body by identifying a location that is a specified distance away from the shadow formed by the ciliary body.

2. The method of claim 1, further comprising:
  forming a scleral tunnel in the scleral tissue of the patient's eye based on the identified position; and
  inserting the scleral prosthesis into the scleral tunnel.

3. The method of claim 1, wherein the illumination provided at the second portion of the patient's eye is provided through an eyelid of the patient and travels under a cornea of the patient's eye to the first portion of the patient's eye.

4. The method of claim 1, wherein:
  identifying the actual location of the ciliary body further comprises identifying an anterior edge of the ciliary body using the shadow; and
  identifying the location that is the specified distance away from the shadow comprises identifying a location that is the specified distance away from the anterior edge of the ciliary body, the location posterior to the anterior edge of the ciliary body.

5. A system comprising:
  eye measurement equipment configured to generate information associated with an actual location of a ciliary body in a patient's eye, the eye measurement equipment comprising an illumination source configured to illuminate a first portion of the patient's eye using illumination provided at a second portion of the patient's eye to create a shadow of the ciliary body in the patient's eye; and
  a controller configured to use the information from the eye measurement equipment to identify a position for a scleral prosthesis to be inserted into scleral tissue of the patient's eye based on the identified location of the ciliary body by identifying a location that is a specified distance away from the shadow of the ciliary body.

6. The system of claim 5, wherein the illumination source is configured to provide the illumination through an eyelid of the patient such that the illumination travels under a cornea of the patient's eye to the first portion of the patient's eye.

7. The system of claim 5, wherein the controller is configured to identify location that is the specified distance away from the shadow by identifying a location that is the specified distance away from an anterior edge of the ciliary body, the location posterior to the anterior edge of the ciliary body.

8. The system of claim 5, further comprising:
  a surgical tool controller configured to control a surgical tool based on the identified position for the scleral prosthesis, the surgical tool configured to form a scleral tunnel in the scleral tissue of the patient's eye.

9. The system of claim 5, further comprising:
  a marking plate assembly configured to place one or more marks on the patient's eye, at least one mark associated with the identified position for the scleral prosthesis.

10. The system of claim 5, wherein the controller comprises a processor and a memory.

11. An apparatus comprising:
a controller configured to identify a position for a scleral prosthesis to be inserted into scleral tissue of a patient's eye, the controller configured to identify the position for the scleral prosthesis using an actual location of a ciliary body in the patient's eye, the actual location of the ciliary body based on a shadow formed by the ciliary body in the patient's eye using an illumination source.

12. The apparatus of claim 11, wherein the controller is configured to receive information identifying the actual location of the ciliary body in the patient's eye from eye measurement equipment.

13. The apparatus of claim 12, wherein the eye measurement equipment comprises the illumination source configured to illuminate a first portion of the patient's eye using illumination provided at a second portion of the patient's eye.

14. The apparatus of claim 13, wherein the information identifying the actual location of the ciliary body in the patient's eye comprises information identifying a location of the shadow produced by the ciliary body.

15. The apparatus of claim 11, wherein the controller is configured to identify the position for the scleral prosthesis by identifying a location that is a specified distance away from an anterior edge of the ciliary body, the location posterior to the anterior edge of the ciliary body.

16. The apparatus of claim 11, wherein the controller is further configured to cause a surgical tool controller to control a surgical tool so as to form a scleral tunnel in the scleral tissue of the patient's eye.

17. A non-transitory computer readable medium embodying a computer program, the computer program comprising:
computer readable program code for receiving information identifying an actual location of a ciliary body in a patient's eye, the actual location of the ciliary body based on a shadow formed by the ciliary body in the patient's eye using an illumination source; and
computer readable program code for identifying a position for a scleral prosthesis to be inserted into scleral tissue of the patient's eye based on the actual location of the ciliary body.

18. The computer readable medium of claim 17, wherein the computer readable program code for receiving the information comprises:
computer readable program code for receiving the information from eye measurement equipment.

19. The computer readable medium of claim 17, wherein the computer readable program code for identifying the position for the scleral prosthesis comprises:
computer readable program code for identifying the position by identifying a location that is a specified distance away from an anterior edge of the ciliary body, the location posterior to the anterior edge of the ciliary body.

20. The computer readable medium of claim 17, wherein the computer program further comprises:
computer readable program code for controlling a surgical tool to form a scleral tunnel in the scleral tissue of the patient's eye at the identified location.

* * * * *